United States Patent [19]

Schott et al.

[11] 4,220,596
[45] Sep. 2, 1980

[54] SEPARATION OF PHTHALIC ANHYDRIDE FROM VAPOR MIXTURE ALSO CONTAINING WATER VAPOR

[75] Inventors: Jeffrey H. Schott; David A. Palmer, both of Naperville; Hobe Schroeder, Warrenville, all of Ill.

[73] Assignee: Standard Oil Company, Chicago, Ill.

[21] Appl. No.: 969,879

[22] Filed: Dec. 15, 1978

[51] Int. Cl.$^2$ ............................................ C07D 307/89
[52] U.S. Cl. ................................................... 260/346.7
[58] Field of Search ...................................... 260/346.7

[56] References Cited

U.S. PATENT DOCUMENTS 2,133,904   10/1938   Reichhold ......................... 260/346.7

Primary Examiner—Henry R. Jiles
Assistant Examiner—Robert C. Whittenbaugh
Attorney, Agent, or Firm—Fred R. Ahlers; William T. McClain; William H. Magidson

[57] ABSTRACT

Water is separated from a mixture of vapors containing 60 to 86 wt. % phthalic anhydride, 5 to 25 wt. % water, 0.8 to 10 wt. % benzoic acid, 0.1 to 4 wt. % o-toluic acid and up to 5 wt. % impurities boiling just above phthalic anhydride (PAN) by a fractionation zone whose reflux liquid is insert to PAN and the aromatic acids and immiscible with water but dissolves PAN at temperatures between its melting and freezing points and also dissolves benzoic acid and o-toluic acid at such temperatures. The reflux liquid or a component thereof when not a single compound leaves the top of the fractionation system as a vapor and does not leave the bottom thereof with PAN. Such water separation technique avoids having PAN vapors in a condenser whose cooled surfaces can and do become coated with solid PAN.

4 Claims, No Drawings

SEPARATION OF PHTHALIC ANHYDRIDE FROM VAPOR MIXTURE ALSO CONTAINING WATER VAPOR

TECHNICAL FIELD

This invention relates to the separation of phthalic anhydride from a vapor mixture containing the anhydride and water vapor by direct contact with a water immiscible heat exchange liquid under conditions such that the anhydride condenses to a liquid and as such is separated from the heat exchange liquid, the water vapors do not condense but are stripped away by vapors of the heat exchange liquid, the mixture of water and heat exchange vapors are cooled to condense both the water and heat exchange liquid and decanting the liquid water, and returning the cooled condensate to the separation system. More particularly the present invention pertains to such separation of water vapor from phthalic anhydride vapor conducted in a distillation zone wherein a heat exchange liquid which boils at a temperature below the boiling temperature of phthalic anhydride and at a temperature above the freezing point temperature of phthalic anhydride is employed as a recycling reflux liquid.

BACKGROUND ART

The problem of separation of phthalic anhydride as a liquid product from a mixture of its vapors and vapors of water has been a problem of long standing and originated with the vapor phase oxidation of naphthalene to produce said anhydride. Such separation of liquid phthalic anhydride from the reaction mixture produced by the vapor phase air oxidation of napthalene, o-xylene and other hydrocarbons oxidizable to phthalic anhydride presented a special situation because such reaction mixture contained only minor volume amounts of phthalic anhydride and water vapors and a major volume amount of air and oxides of carbon. Such reaction mixture was produced at temperatures in the range of from 315° C. up to 635° C. and required liquid phthalic anhydride to be recovered under conditions at which all or a substantial portion of the anhydride remained uncondensed in the vapor state at the melting temperature of the anhydride and at which the partial pressure of the anhydride vapor would be less than the vapor pressure of the anhydride in equilibrium with liquid anhydride at its melting point.

U.S. Pat. No. 2,702,091 describes three commercially used methods for recovery of phthalic anhydride from such mixtures under such difficult conditions. One method makes use of large air cooled chambers upon whose inner surfaces long crystals of phthalic anhydride adhere. Such chambers were referred to as "hay barn" condensers. Such hay barn condensers ordinarily separated only 80 to 90% of the anhydride and their efficiency decreased as hard adherent scale formed on the inner walls.

The second method involved a tube and shell heat exchanger cooled on the tube side by a heat exchange liquid so that phthalic anhydride condensed as a solid in the shell side. By the use of such condensers or train of such condensers in parallel flow, one such condenser or train of such condensers may be cooled and on stream while the other such condenser or train of condensers are heated to melt the solidified anhydride.

The third method involved the use of water scrubbing of the gaseous reaction mixture but this method produced a solution of o-phthalic acid which had to be concentrated and the dicarboxylic acid dehydrated back to the anhydride.

U.S. Pat. No. 2,702,091 discloses as a solution to the even then long standing problem described above the condensation of phthalic anhydride from the unique mixtures existing under difficult to process conditions by the use of a moving bed of solid inorganic heat exchange particles whereby the bed has a temperature gradient ranging from a temperature below the melting point of the anhydride at the upper portion of the downwardly moving bed to a temperature above about 205° C. in its lower portion into which the gaseous mixture is introduced, withdrawing from above the upper portion of the bed a cool gaseous stream, and withdrawing from an intermediate portion of the bed a gas mixture containing phthalic anhydride vapor at a concentration such that the anhydride's dew point is higher than the melting point of phthalic anhydride. The anhydride-containing gas mixture withdrawn can be readily cooled to condense a liquid product.

U.S. Pat. No. 4,071,540 reviews the history of proposed organic absorbent techniques for recovery of phthalic anhydride or maleic anhydride from the unique mixtures existing under difficult to process conditions. Such organic absorbents included dibutyl phthalate, melted wax, diphenyl-pentachloride, tricresyl phosphate, dibutylmaleate, dimethylterephthalate, as well as other dialkylphthalates, alkyl or alkenyl succinic anhydrides, and dimethylbenzophenones. Said U.S. Pat. No. 4,071,540 proposes the use of polymethylbenzophenones having a total of 2 to 5 methyl groups on the two rings, preferably the dixylyl ketones as the organic absorbent in an absorption process or absorber column. Such a process is illustrated as a combination of an absorber column and a stripping column. In the absorber column downwardly moving cool absorbent scrubs anhydride from the gas introduced into the bottom. Substantially anhydride free gas exits the top. The absorbent-anhydride mixture is transferred into the upper portion of the stripping column which has a reboiler to supply the heat for deabsorption of anhydride. The anhydride-free liquid absorbant flows down the stripper column and is transferred through a cooler into the absorber column. The anhydride product exits the top of the stripping column.

The present problem also involves the separation and recovery of phthalic anhydride from a vapor mixture containing the phthalic anhydride vapor but the present problem is distinctly different because such vapor mixture additionally contains from 10 up to 35 weight percent of water vapor. Such vapor mixture is not a direct product of an oxidation process. Rather such mixture is generated by the dehydration-evaporation process conducted at a pressure of 760 mm Hg to 40 mm Hg and a temperature of from 180° C. up to 235° C. with a feed which is the liquid product of the neat (no extraneous reaction solvent or diluent) catalytic oxidation of liquid o-xylene with air at a temperature of from 150° C. up to 235° C., under a gauge pressure of from 17 up to 30 kg/cm², and in the presence of catalysis provided by HBr or Br$_2$ in combination with a source of cobalt and manganese ions. Generally the catalyst components are employed in the amounts of 0.3 to 10 milligram atoms of cobalt and from 0.06 up to 20 milligram atoms of manganese per gram mole of o-xylene. The amount of bromine used is in the range of from at least 0.5 but less than 2 milligram atoms per gram atom total of cobalt and manganese. Small amounts of benzoic acid added per se or as toluene or of acetic acid are used to minimize total combustion of o-xylene or as a phase miscibility agent to make miscible otherwise immiscible liquid o-xylene and liquid o-phthalic acid which retains the catalyst components in solution. The success, i.e., high conversion of o-xylene and high yield of o-phthalic acid, of said catalytic oxidation of liquid o-xylene with air is dependent upon the maintenance of the combination of temperature, pressure and liquid water content of the reaction mixture to minimize and or substantially prevent the formation of phthalic anhydride by dehydration of o-phthalic acid.

The conduct of such neat oxidation of liquid o-xylene under batchwise and modified batchwise having a short period of continuous o-xylene feed is disclosed in U.S. patent application Ser. No. 867,050 filed Jan. 5, 1978; under one-step continuous oxidation is disclosed in U.S. patent application Ser. No. 961,763, filed Nov. 17, 1978; and under continuous oxidation in two-steps interconnected for series flow therethrough is disclosed in U.S. patent application Ser. No. 50,159, filed June 20, 1979.

Typical liquid reaction effluent compositions from such batchwise, modified batchwise, continuous one step, and continuous two series connected steps are shown in TABLE I which follows.

TABLE I

TYPICAL COMPOSITIONS OF LIQUID EFFLUENTS FROM NEAT OXIDATION OF LIQUID ORTHO-XYLENE

| Components, wt% | I | II | III | IV | V |
|---|---|---|---|---|---|
| o-Phthalic Acid | 88.8 | 91.9 | 76.0 | 71.0 | 91.9 |
| o-Toluic Acid | 0.57 | 0.24 | 1.92 | 1.05 | 1.03 |
| Phthalide | 1.05 | 0.10 | 1.92 | 1.22 | 0.54 |
| 2-Carboxybenzaldehyde | 0 | 0.90 | 0.13 | 0.22 | 0.50 |
| Benzoic Acid | | | | | 0.35 |
| (Acetic Acid) | — | 0.6 | 11.2 | (3–4) | 0.81 |
| High Boilers* | 3.51 | 1.36 | 2.89 | 2.17 | 1.79 |
| Water | 5.0 | 4.9 | 5.75 | 20.5 | 3.45 |

*Compounds boiling at higher temperature than phthalic anhydride including organo-metallic (catalyst metals) compounds and oxygen-containing aromatic compounds.

Under certain conditions the neat oxidation process conducted continuously using a miscibility agent (e.g. 5 to 20% of benzoic acid or acetic acid as miscibility agent) and air enriched to 50 volume % $O_2$ by mixing with oxygen gas can tolerate for commercially acceptable oxidation rate as much as 21 weight percent water. Otherwise for neat air oxidation of liquid o-xylene there is needed at least one weight percent free liquid water but not more than 8 weight percent free liquid water. The minimum 2 wt% water is needed for catalytic activity acceptable for commercial use. Above the 8 weight percent maximum, the reaction becomes increasingly sluggish and at about 9 to 10 weight percent water in the reaction mixture the oxidation ceases.

The above liquid oxidation effluents are processed to dehydrate o-phthalic acid to phthalic anhydride. This is preferably done by subjecting the liquid oxidation effluent to dehydration-evaporation conducted at a temperature of from 180° C. up to 235° C. and a pressure of from 760 mm Hg down to 40 mm Hg. Under such conditions a mixture of vapors comprising, on a weight basis, 60 to 86% phthalic anhydride, 0.8 to 10% benzoic acid, 0.1 to 4% o-toluic acid, 0.2 to 3.5% other oxygen-containing aromatic compounds (phthalide, 2-carboxybenzaldehyde and a small amount of the high boilers including bromine containing compounds), and from 5% up to 25% water. Such vapor mixture contains about 85–86% of the phthalic anhydride equivalent o-phthalic acid content of the liquid oxidation effluent as well as about 10–15% of its bromine content, 25–26% of its o-toluic acid content, substantially all of its phthalide, 60 to 70% of its benzoic acid, and 8–10% of its high boilers. Such a mixture of vapors with its rather high, 60 to 85 weight percent, phthalic anhydride vapor content and also rather high, 10 to 25 weight percent, water content differs materially from the phthalic anhydride or maleic anhydride containing compositions previously considered for separation and recovery of the anhydride. Such prior compositions contained from about one to about four weight percent maleic anhydride or from about three to about four weight percent phthalic anhydride.

In view of such considerable differences between the vapor mixture originating from the product of the neat oxidation of liquid o-xylene and the vapor-gas mixture originating from the vapor phase oxidations to produce maleic anhydride or phthalic anhydride, the prior art processes for separation of maleic anhydride or phthalic anhydride from vapor-gas mixtures lean in content of such anhydrides do not have any real teaching value with respect to separating phthalic anhydride from our vapor mixture very rich in said anhydride and also of relatively high water content. Also no pertinent prior art process could be found which was concerned with separation and recovery of phthalic anhydride from such vapor mixture rich in phthalic anhydride content and also having a high water content.

However, we did conceive a separation process applicable to such vapor mixture rich in phthalic anhydride vapor which uniquely makes use of the principles of fractionation and solvent scrubbing wherein the scrubbing solvent also functions as the liquid reflux from the rectification zone down through the stripping zone.

DESCRIPTION OF THE INVENTION

Our concept for the separation of phthalic anhydride from a vapor mixture containing 60 to 85 weight percent of said anhydride and 25 to 10 weight percent water vapor with the remainder comprising vapors of benzoic acid, o-toluic acid and materials boiling near or just above said anhydride involves contacting such vapor mixture in countercurrent flow with a reflux liquid at a temperature below the boiling point of phthalic anhydride to condense it and dissolve its condensate. Said separation is effected by exchange of heat from the vapor mixture to vaporize some of the reflux liquid. Its vapors and water vapor move upward in a rectification zone countercurrent to the flow of reflux liquid and form a vapor mixture enriched in water vapor and vapor of the reflux liquid but depleted in vapors of benzoic acid, toluic acid and aromatic compounds having boiling temperatures above that of water but below such acids. Such enrichment in water vapor and vapors of reflux liquid continues until the rising vapor mixture contains substantially only vapors of water and the reflux liquid. The mixture of substantially only vapors of water and reflux liquid is cooled to a temperature below the boiling temperature of water, thereby condensing both the reflux liquid and water. The water condensate separates from the reflux liquid's condensate. The water layer is discarded. The cool reflux liquid condensate layer is recycled to said rectification separation.

The reflux liquid moves from the rectification down through said contact with the feed vapor mixture to a stripping zone wherein the reflux liquid carrying phthalic anhydride condensate as dissolved liquid and or solvent becomes enriched with respect thereto and with respect to benzoic and o-toluic acids and phthalide. The reflux liquid containing phthalic anhydride, benzoic acid, o-toluic acid and pthalide is heated to a temperature which vaporizes the reflux liquid but not phthalic anhydride rather the heating leaves the anhydride as a liquid in which the phthalide, benzoic acid and o-toluic acid become dissolved.

Such a concept requires as the reflux liquid a substantially pure single compound or a mixture of boiling point related compounds so that there is no component of the reflux liquid which will remain with and contaminate phthalic anhydride. The reflux liquid must be an inert solvent or absorbant for phthalic anhydride, benzoic acid, and o-toluic acid at low temperatures, e.g. below the anhydride's freezing point, and miscible with said benzene carboxylic acids at higher temperatures between their melting and boiling point temperatures. The reflux liquid must be immiscible and unreactive with water to facilitate their separation for recycle of the reflux liquid and minimize its loss in the separated water condensate. The reflux liquid must have a vapor pressure higher than the vapor pressure of phthalic anhydride to be readily separable therefrom but sufficiently low to remain substantially liquid after contact with the hot, 180° to 235° C. feed, and move through the stripping zone. Lastly, the reflux liquid should not form an azeotrope with either one or all of phthalic anhydride, benzoic acid or o-toluic acid.

The most convenient use of such reflux liquid is in a combination of a rectification zone above a feed zone, a stripping zone below the feed zone, a zone for vaporizing the reflux liquid at a temperature above the melting point but below the boiling point temperatures of phthalic anhydride and transfering the reflux liquids vapors to contact the reflux liquid carrying in solution or by absorption phthalic anhydride, benzoic acid and o-toluic acid, and a zone to receive and cool the mixture of water and reflux liquid vapors to condense them for their separation and recyle of the reflux liquid condensate. Said combination of condensation zone, rectification zone, feed zone, stripping zone and reboiling zone define, of course, a fractionation system.

Methylbenzoate is the preferred reflux liquid to use in the fractionation system for effectively removing water vapor from a mixture thereof with vapors of phthalic anhydride, benzoic acid, o-toluic acid and phthalide.

One example of such fractionation system is provided by a top recycle tray, a 15 tray Oldershaw column for rectification zone below the recycle tray, a feed tray below the rectification zone, and a twenty-tray Oldershaw column as the stripping zone below the feed tray. Both of said columns have internal diameters of 28 mm and are vacuum jacketed as are the feed and recycle trays. A two liter flask having a side outlet for liquid removal and heated by a mantle heated electrically served as a reboiler. Such mantle heating is controlled by varying the electric current supplied to the mantle. The feed tray, stripping column and reboiler are in a heated enclosure maintained at 145° C. The rectification column and reflux tray are in a chamber maintained at 29° C.

As it will be appreciated by a chemical process design engineer, such fractionation system towers or columns can be any of the trayed or packed column generally useful for fractionation.

Vapor from above the recycle tray is transfered through a heat traced line to a condenser cooled to a temperature of from 25° up to 43° C. above a decanter from the side of which the top aqueous phase flowed into a receiver and from the bottom of which the reflux liquid condensate returned through a reflux control valve and meter. A water cooled knockback condenser is in the vacuum line to minimize removal of low boiling compounds into the vacuum system. Pressure at the top of the rectification column is maintained at 150 torr by a control valve operated by a pneumatic controller and an absolute pressure transmitter.

After charging 800 grams methylbenzoate to the decanter and 250 grams to the reboiler of water free composition otherwise corresponding to the feed to the system, the pressure controller is adjusted to 150 torr, the reboiler is heated, the heating chambers were heated to 145° C. and 29° C. and coolants were supplied to the condensers associated with the decanter. After boiling had begun in the reboiler, methylbenzoate flow at 4 ml/min from the decanter to the column was begun. The system was permitted to operate at total reflux until the temperatures of the reboiler, of the liquid on the feed tray and the reflux tray had stabilized. Feed was supplied at 5.5 gm/min and methylbenzoate flow was adjusted to prevent flooding of the column. Again the system was permitted to operate first until temperatures (reboiler, feed tray and reflux tray) and flow rates stabilized and then product (bottoms liquid from reboiler) and water condensate were withdrawn at rates adjusted to reach steady state conditions. Samples of product were taken for analysis after at least one hour of steady state operation.

Organic components were determined by esterification gas chromatography and bromine content was determined by x-ray fluorescence.

The pressure in the reboiler is 202.5 torr for column top (above reflux tray) pressure of 150 torr. Pure phthalic anhydride has a calculated boiling point temperature of 230° C. at 203.5 torr. The reboiler temperature of 230° C. for Examples 1, 2, 3 and 4 (instead of the desired 205° C.) enhanced, as the data for those examples will show, the removal of benzoic acid and o-toluic acid from the product. As will be noted from the data of Examples 5 and 6, the reboiler temperature of 215° C. removed less of the benzoic acid and o-toluic acid from the product. However, although the material balances (accountability), on benzoic acid and o-toluic acid are not satisfactory, the system retention is about 60 grams and could contain the 41 grams of benzoic acid and o-toluic acid not accounted for in Example 5. Unfortunately such system retained materials were not analyzed for each example.

TABLES II and III to follow will provide the pertinent operating data for the illustrations of the practice of the present invention and the results produced thereby.

TABLE II

| SEPARATION OF PHTHALIC ACID AND WATER | | | |
|---|---|---|---|
| Feed Composition: | Example 1 | Example 2 | Example 3 |
| Phthalic Anhydride wt% | 75.2 | 83.6 | 84.6 |
| Benzoic Acid, wt% | 9.92 | 5.98 | 6.04 |
| o-Toluic Acid, wt% | 4.36 | 1.16 | 1.17 |
| Water, wt% | 6.15 | 7.10 | 6.43 |
| Other[1], wt% | 3.67 | 1.58 | 1.94 |

TABLE II-continued
SEPARATION OF PHTHALIC ACID AND WATER

| Feed Composition: | Example 1 | Example 2 | Example 3 |
|---|---|---|---|
| Feed Rate, g/min. | 4.475 | 3.875 | 4.275 |
| Reflux Rate MB,[2] ml/min | 5.0 | 4.1 | 4.0 |
| Reflux Ratio ml MB/ml H$_2$O | 18.2 | 14.9 | 14.6 |
| Reboiler Temperature, °C. | 230 | 230 | 230 |
| Product Composition | | | |
| Phthalic Anhydride, wt% | 86.1 | 93.9 | 94.1 |
| Benzoic Acid, wt% | 5.25 | 0.49 | 3.39 |
| o-Toluic Acid, wt% | 3.75 | 1.62 | 1.03 |
| Other[1], wt% | 3.09 | 2.64 | 2.02 |

[1]"Other" includes phthalide, bromine and compounds boiling just above phthalic anhydride.
[2]"MB" is methylbenzoate.

TABLE III
SEPARATION OF PHTHALIC ANHYDRIDE AND WATER

| Feed Composition | Example 4 | Example 5 | Example 6 |
|---|---|---|---|
| Phthalic Anhydride, wt% | 86.8 | 78.6 | 76.4 |
| Benzoic Acid, wt% | 4.9 | 8.29 | 8.4 |
| o-Toluic Acid, wt% | 0.12 | 2.63 | 2.65 |
| Water, wt% | 7.90 | 9.09 | 9.43 |
| Other[1], wt% | 0.73 | 0.92 | 0.83 |
| Feed Rate, g/min | 3.475 | 5.5 | 5.3 |
| Reflux Rate MB[2] ml/min | 4.0 | 4.0 | 4.0 |
| Reflux Ratio ml MB/ml H$_2$O | 14.6 | 8.0 | 8.0 |
| Reboiler Temperature, °C. | 230 | 215 | 215 |
| Product Composition: | | | |
| Phthalic Anhydride, wt% | 98.7 | 96.9 | 95.3 |
| Benzoic Acid, wt% | 0.09 | 0.15 | 0.56 |
| o-Toluic Acid, wt% | 0.06 | 0.49 | 1.53 |
| Other[1] | 1.59 | 0.84 | 0.94 |

[1]"Other" includes phthalide, bromine and components boiling just higher than phthalic anhydride.
[2]"MB" is methylbenzoate.

In TABLES IV and V to follow there are compared the component contents of Feed (F) and Product (P) and the totals of the components. The Feed components are on a water free basis for better comparison with Product components. The totals of components of Feed and Product are an indication of efficiency of the process:

TABLE IV

| | Example 1 | |
|---|---|---|
| Component, wt% | Feed | Product |
| Phthalic Anhydride | 80.1 | 86.1 |
| Benzoic Acid | 10.57 | 5.25 |
| o-Toluic Acid | 4.64 | 3.75 |
| Other[1] | 3.91 | 3.09 |
| Total: | 99.22 | 98.19 |
| | Example 2 | |
| Component, wt% | Feed | Product |
| Phthalic Anhydride | 90.1 | 93.9 |
| Benzoic Acid | 6.44 | 0.49 |
| o-Toluic Acid | 1.25 | 1.62 |
| Other[1] | 1.70 | 2.64 |
| Total: | 99.39 | 98.65 |
| | Example 3 | |
| Component, wt% | Feed | Product |
| Phthalic Anhydride | 90.4 | 94.1 |
| Benzoic Acid | 6.46 | 3.39 |
| o-Toluic Acid | 1.25 | 1.03 |
| Other[1] | 2.07 | 2.02 |
| Total: | 100.15 | 100.54 |

[1]"Other" see TABLES II and III

TABLE V

| | Example 4 | |
|---|---|---|
| Component, wt% | Feed | Product |
| Phthalic Anhydride | 94.2 | 98.7 |
| Benzoic Acid | 5.32 | 0.09 |
| o-Toluic Acid | 0.13 | 0.06 |
| Other[1] | 0.79 | 1.59 |
| Total: | 100.44 | 100.44 |
| | Example 5 | |
| Component, wt% | Feed | Product |
| Phthalic Anhydride | 86.4 | 96.9 |
| Benzoic Acid | 9.12 | 0.15 |
| o-Toluic Acid | 2.89 | 0.49 |
| Other[1] | 1.01 | 0.84 |
| Total: | 99.42 | 98.38 |
| | Example 6 | |
| Component, wt% | Feed | Product |
| Phthalic Anhydride | 84.3 | 95.3 |
| Benzoic Acid | 9.27 | 0.56 |
| o-Toluic Acid | 2.92 | 1.53 |
| Other[1] | 0.92 | 0.94 |
| Total: | 97.41 | 98.33 |

[1]"Other" see TABLES II and III

By comparison of the results of Example 1 against the results of the other five examples it will be noted that as the Reflux rate of methylbenzoate recycled to the system decreases there are greater amounts of benzoic and o-toluic acids removed from the feed. While this may seem to be desirable with respect to effecting a more complete separation of phthalic anhydride from attendant impurities, this is not a favorable result when those components may ultimately be in the water condensate to be discarded and its benzene carboxylic acids content would raise a question of surface water pollution. It is better to retain those benzene monocarboxylic acids in the phthalic anhydride product and later remove them as a low boiling first fraction and recycle the same to the o-xylene oxidation for the benefits benzoic acid there provides (e.g. diminishes o-xylene over combustion and overcomes formation of liquid o-xylene phase and liquid phthalic acid phase) and also complete the oxidation of o-toluic acid to o-phthalic acid.

It appears that a more favorable reflux volume ratio of methylbenzoate to water, for example, 20 to 25 volumes of methylbenzoate per volume of water at a reboiler temperature of 230° C. and pressure of 150 torr would help keep the benzoic acid and o-toluic acid with the phthalic anhydride product. Likewise at a reboiler temperature of 215° C. and pressure of 150 torr, the more favorable of said volume reflux ratio would more likely be in the range of 14:1 to 20:1 rather than 8:1 used.

In TABLE VI to follow there is presented a more complete material balance showing the distribution of components of the feed to the anhydride product, water removed and retained in the methylbenzoate reflux liquid as a result of the process of Example 5.

TABLE VI
MATERIAL BALANCE: COMPONENT DISTRIBUTION BY PROCESS OF EXAMPLE 5

| | Benzoic Acid | o-Toluic Acid | Phthalic Anhydride | Br₂ |
|---|---|---|---|---|
| Feed 1385 grams | 126.3g | 40.0g | 1196.6g | 1.52g |
| Product 1208 grams | 1.8g | 5.9g | 1170.3g | 0.79g |
| Water 125 grams | — | — | — | 0.39g |
| Methylbenzoate, 967 grams | 91.4g | 26.3g | 36.3g | 0.19g |
| Total Grams Recovered | 93.2 | 32.2 | 1206.6 | 1.37 |
| Accountability | 74% | 81% | 101% | 90% |

The above material balance indicates that the missing 26% of original benzoic acid and 19% of o-toluic acid did not enter the water condensate decanted and those acids did not enter the methylbenzoate collected in the decanter. The missing benzoic and o-toluic acids may, as mentioned before, be in the liquid retained on the trays of the columns used.

Finally, it will be of importance to the design engineer for selection of materials of construction for the fractionation system to understand the distribution of bromine among the liquids withdrawn and reflux liquid retained. This will be shown in TABLE VII to follow for Examples 3, 5 and 6.

TABLE VII
BROMINE CONCENTRATION, ppm by weight

| | Example 3 | Example 5 | Example 6 |
|---|---|---|---|
| Feed | 737 | 1100 | 1100 |
| Product | 437 | 653 | 574 |
| Water | 1200 | 3100 | 3900 |
| Methylbenzoate* | 175 | 194 | — |

*Methylbenzoate in decanter

Preferably the process of this invention is conducted at a reboiler temperature of from 200 to 230° C. and pressure of from 150 to 200 torr with a methylbenzoate to water reflux ratio of from 8:1 up to 30:1.

To provide a commercially attractive sequence of steps from neat oxidation of liquid o-xylene there must be a high conversion of xylene and high yield of product, a simple means for obtaining partially purified phthalic anhydride, and an efficient way to remove phthalide before the final anhydride purification by fractionation. As mentioned before the oxidation process of the indicated copending applications is one key step because it provides substantially complete conversion of o-xylene and yields of 80 to 90 mole percent and above, of o-phthalic acid by the expedient of preventing said dicarboxylic acid from dehydrating to its anhydride in the reaction mixture. Converting o-phthalic acid from said oxidation to partially purified anhydride product by the combination of the dehydration-evaporation technique followed by the present separation of water from the anhydride are other key steps to a commercially attractive process. Lastly the remaining key step is the removal of phthalide from the phthalic anhydride product of this invention by heating it to its reflux temperature for 2 to 8 hours in the presence of a uniquely acting chemical addition agent which makes phthalide per se not existent in the refluxing liquid probably by converting it to a rather high molecular weight derivative.

The invention claimed is:

1. The method of separation of water, from 0 up to substantially all of the benzoic acid and from 0 up to about 55 weight percent of the o-toluic acid from a mixture of vapors which is at a temperature of from 180° C. up to 235° C. and a pressure of 760 mmHg to 100 mmHg wherein said mixture contains from 60% up to 86% phthalic anhydride, from 5% to 25% water, from 0.8% up to 10% benzoic acid, from 0.1% up to 4% o-toluic acid and up to 5% of compounds boiling at a temperature just above the boiling temperature of phthalic anhydride thereby leaving phthalic anhydride together with the remainder of benzoic acid, toluic acid and said compounds boiling just above phthalic anhydride as the phthalic anhydride product; which separation method is accomplished by the flow of fluids in a combination of zones including a rectifying zone above and a stripping zone below a contact zone which is in flow communication with both the rectifying zone and the stripping zone, a heating zone below and in fluid flow communication with the bottom of the stripping zone, a cooling zone in vapor flow communication with the top of the rectifying zone and in liquid flow communication with a single zone for both separating a liquid water layer and an immiscible liquid layer, decanting the water layer and recycling the immiscible liquid to the top of the rectification zone; by imposing a reduced pressure of from 50 to 150 mmHg on the cooling zone which by presure drop through the liquid in the rectifying, contacting and stripping zones imposes a pressure of from 100 to 250 mmHg on the heating zone; by introducing said 180° to 235° temperature vapor mixture into the contacting zone wherein phthalic anhydride vapor is cooled to the liquid state by direct heat exchange with downwardly flowing cooler reflux liquid thereby vaporizing a portion of the reflux liquid; which reflux liquid is immiscible with and inert to water; is an inert solvent or absorbent for phthalic anhydride, o-toluic acid and benzoic acid at a temperature down to the freezing point of phthalic anhydride; is miscible with o-toluic and benzoic acids at temperatures between their melting and boiling temperature; has a vapor pressure sufficiently above the vapor pressure of phthalic anhydride to effect their distillative separation but sufficiently low so as to be present in the liquid phase in the stripping zone; which does not form an azeotrope with phthalic anhydride, o-toluic acid or benzoic acid; and which is a single compound or a mixture of boiling point related compounds such that no component of said related compounds will remain with and contaminate phthalic anhydride; by contacting in the retifying zone the upwardly moving vapor of reflux liquid, water, o-toluci acid and benzoic acid with reflux liquid in the liquid state to cool said acids to a temperature between their melting and boiling temperatures, thereby dissolving or absorbing said acids in concentrations increasing with the downward movement of the liquid state of the reflux liquid and increasing the concentration of water vapor in the upwardly moving vapors of the reflux liquid; by withdrawing the mixture of water and reflux liquid vapors from above the cool reflux liquid's entrance into the rectifying zone; by charging the withdrawn vapor mixture to the cooling zone operated at a temperature between boiling and freezing temperature of water at 50 to 150 mmHg to cool the vapors of water and reflux liquid to the liquid state for their flow into the separation-decantation zone for discard of the liquid water and recycle of cool liquid state of reflux liquid to the top of the rectifying zone; by maintaining the heating zone at a temperature of from 200° C. up to 230° C. to vaporize a portion of the liquid phthalic anhydride product flowing into the heating zone from the stripping zone to provide said zone the heat by heat exchange between the phthalic anhydride product vapors and the reflux liquid in the stripping zone to separate in the bottom portion thereof vaporized reflux liquid for upward flow therein, and liquid phthalic anhydride product for downward flow therein to the heating zone; and by withdrawing a portion of the liquid phthalic anhydride product from the heating zone.

2. The method of claim 1 wherein the reflux liquid is methylbenzoate.

3. The method of claim 2 wherein the pressure in the separating-decanting zone is 150 mmHg and the pressure in the heating zone is 200 to 205 mmHg.

4. The method of claim 3 wherein the cooled liquid state of reflux liquid returned to the stripping zone is at the rate of 5 to 30 ml per equivalent of 1.0 ml of water in the vapor states in the rectifying zone.

* * * * *